US011869185B2

(12) United States Patent
Ceballos Lentini et al.

(10) Patent No.: US 11,869,185 B2
(45) Date of Patent: Jan. 9, 2024

(54) SYSTEMS AND METHODS FOR PROCESSING IMAGES TO PREPARE SLIDES FOR PROCESSED IMAGES FOR DIGITAL PATHOLOGY

(71) Applicant: PAIGE.AI, Inc., New York, NY (US)

(72) Inventors: Rodrigo Ceballos Lentini, Flemington, NJ (US); Christopher Kanan, Pittsford, NY (US); Patricia Raciti, New York, NY (US); Leo Grady, Darien, CT (US); Thomas Fuchs, New York, NY (US)

(73) Assignee: Paige.AI, Inc., New York, NY (US)

( * ) Notice: Subject to any disclaimer, the term of this patent is extended or adjusted under 35 U.S.C. 154(b) by 0 days.

(21) Appl. No.: 17/804,123

(22) Filed: May 26, 2022

(65) Prior Publication Data

US 2022/0293251 A1 Sep. 15, 2022

Related U.S. Application Data

(63) Continuation of application No. 17/654,614, filed on Mar. 14, 2022, now Pat. No. 11,676,274, which is a
(Continued)

(51) Int. Cl.
*G06T 7/00* (2017.01)
*G16H 50/20* (2018.01)
(Continued)

(52) U.S. Cl.
CPC .......... *G06T 7/0012* (2013.01); *G06F 18/214* (2023.01); *G16H 30/40* (2018.01);
(Continued)

(58) Field of Classification Search
CPC .. G06V 10/449; G06V 40/107; G06F 18/214; A61B 5/165; G01R 33/5608; H04N 23/673

See application file for complete search history.

(56) References Cited

U.S. PATENT DOCUMENTS 6,058,322 A 5/2000 Nishikawa et al.
6,396,953 B1 5/2002 Abbey
(Continued)

FOREIGN PATENT DOCUMENTS

CN 101004412 A 7/2007
CN 103207105 A 7/2013
(Continued)

*Primary Examiner* — Yosef Kassa
(74) *Attorney, Agent, or Firm* — Bookoff McAndrews, PLLC

(57) ABSTRACT

Systems and methods are disclosed for processing an electronic image corresponding to a specimen. One method for processing the electronic image includes: receiving a target electronic image of a slide corresponding to a target specimen, the target specimen including a tissue sample from a patient, applying a machine learning system to the target electronic image to determine deficiencies associated with the target specimen, the machine learning system having been generated by processing a plurality of training images to predict stain deficiencies and/or predict a needed recut, the training images including images of human tissue and/or images that are algorithmically generated; and based on the deficiencies associated with the target specimen, determining to automatically order an additional slide to be prepared.

20 Claims, 8 Drawing Sheets

Related U.S. Application Data continuation of application No. 17/346,923, filed on Jun. 14, 2021, now Pat. No. 11,309,074, which is a continuation of application No. 17/137,769, filed on Dec. 30, 2020, now Pat. No. 11,062,801, which is a continuation of application No. 16/884,978, filed on May 27, 2020, now Pat. No. 10,937,541.

(60) Provisional application No. 62/853,383, filed on May 28, 2019.

(51) Int. Cl.
  G16H 30/40 (2018.01)
  G06F 18/214 (2023.01)

(52) U.S. Cl.
  CPC ... G16H 50/20 (2018.01); *G06T 2207/10056* (2013.01); *G06T 2207/20081* (2013.01); *G06T 2207/30024* (2013.01); *G06T 2207/30096* (2013.01); *G06V 2201/03* (2022.01)

(56) References Cited

U.S. PATENT DOCUMENTS

| | | | |
|---|---|---|---|
| 6,855,114 B2 | 2/2005 | Drukker et al. | |
| 6,968,327 B1 | 11/2005 | Kates et al. | |
| 7,514,444 B2 | 4/2009 | Honigberg et al. | |
| 7,524,061 B2 | 4/2009 | Yan et al. | |
| 7,774,060 B2 | 8/2010 | Westenskow et al. | |
| 8,008,431 B2 | 8/2011 | Weinschenk et al. | |
| 8,119,139 B2 | 2/2012 | Weinschenk et al. | |
| 8,131,475 B2 | 3/2012 | Staudt et al. | |
| 8,396,817 B2 * | 3/2013 | Yokono | G09B 19/00 434/155 |
| 8,409,799 B2 | 4/2013 | Young et al. | |
| 8,454,507 B2 | 6/2013 | Tremper et al. | |
| 8,465,289 B2 * | 6/2013 | Kameyama | A61B 5/165 434/236 |
| 8,488,864 B2 | 7/2013 | Norimatsu | |
| 8,494,258 B2 * | 7/2013 | Yokono | G06V 10/449 382/103 |
| 8,507,445 B2 | 8/2013 | Arap et al. | |
| 8,510,054 B2 | 8/2013 | Iwatani et al. | |
| 8,513,212 B2 | 8/2013 | Conklin et al. | |
| 8,582,806 B2 * | 11/2013 | Yokono | G06V 10/449 382/103 |
| 8,609,437 B2 | 12/2013 | Yeung et al. | |
| 8,747,855 B2 | 6/2014 | Reiter et al. | |
| 8,787,638 B2 | 7/2014 | Zee et al. | |
| 8,798,345 B2 | 8/2014 | Sasaki et al. | |
| 8,877,445 B2 | 11/2014 | Shackney | |
| 8,936,555 B2 | 1/2015 | Tremper et al. | |
| 8,961,985 B2 | 2/2015 | Weinschenk et al. | |
| 9,159,129 B2 | 10/2015 | Schoenmeyer et al. | |
| 9,211,096 B2 | 12/2015 | Tremper et al. | |
| 2013/0071002 A1 | 3/2013 | Otsuka et al. | |

FOREIGN PATENT DOCUMENTS

| | | |
|---|---|---|
| CN | 105027165 A | 11/2015 |
| CN | 107064019 A | 8/2017 |
| CN | 107368670 A | 11/2017 |
| CN | 108717554 A | 10/2018 |
| CN | 109253904 A | 1/2019 |
| CN | 109416730 A | 3/2019 |
| JP | 2016520814 A | 7/2016 |
| JP | 2019513228 A | 5/2019 |
| JP | 7012731 B2 | 2/2022 |
| WO | 2017130790 A1 | 8/2017 |
| WO | 2017221592 A1 | 12/2017 |
| WO | 2018188023 A1 | 10/2018 |
| WO | 2019026081 A2 | 2/2019 |
| WO | 2020075172 A1 | 4/2020 |

\* cited by examiner

200

202 — RECEIVING A TARGET ELECTRONIC IMAGE OF A SLIDE CORRESPONDING TO A TARGET SPECIMEN, THE TARGET SPECIMEN COMPRISING A TISSUE SAMPLE OF A PATIENT

204 — APPLYING A MACHINE LEARNING MODEL TO THE TARGET ELECTRONIC IMAGE TO DETERMINE DEFICIENCIES ASSOCIATED WITH THE TARGET SPECIMEN, THE MACHINE LEARNING MODEL HAVING BEEN GENERATED BY PROCESSING A PLURALITY OF TRAINING IMAGES TO PREDICT STAIN DEFICIENCIES AND/OR PREDICT A NEEDED RECUT, THE TRAINING IMAGES COMPRISING IMAGES OF HUMAN TISSUE AND/OR IMAGES THAT ARE ALGORITHMICALLY GENERATED

206 — BASED ON THE DEFICIENCIES ASSOCIATED WITH THE TARGET SPECIMEN, DETERMINING TO AUTOMATICALLY ORDER AN ADDITIONAL SLIDE TO BE PREPARED

*FIG. 2*

SYSTEMS AND METHODS FOR PROCESSING IMAGES TO PREPARE SLIDES FOR PROCESSED IMAGES FOR DIGITAL PATHOLOGY

RELATED APPLICATION(S)

This patent application is a continuation of and claims the benefit of priority to U.S. application Ser. No. 17/654,614, filed on Mar. 14, 2022, which is a continuation of U.S. application Ser. No. 17/346,923 (now U.S. Pat. No. 11,309,074), filed on Jun. 14, 2021, which is a continuation of U.S. application Ser. No. 17/137,769 (now U.S. Pat. No. 11,062,801), filed Dec. 30, 2020, which is a continuation of U.S. application Ser. No. 16/884,978 (now U.S. Pat. No. 10,937,541), filed May 27, 2020, which claims priority to U.S. Provisional Application No. 62/853,383, filed May 28, 2019, each of which are incorporated herein by reference in their entirety.

FIELD OF THE DISCLOSURE

Various embodiments of the present disclosure pertain generally to pathology slide preparation and related image processing methods. More specifically, particular embodiments of the present disclosure relate to systems and methods for identifying or detecting slides lacking information sufficient to provide a diagnosis based on processing images of tissue specimens. The present disclosure further provides systems and methods for automatically ordering additional slides that may contain data sufficient to provide a diagnosis based on processing images of tissue specimens.

BACKGROUND

Pathology specimens may be cut into multiple sections, prepared as slides, and stained for a pathologist to examine and render a diagnosis. When uncertain of a diagnostic finding on a slide, a pathologist may order additional cut levels, stains, or other tests to gather more information from the tissue. Technicians may then create new slides which may contain additional information for the pathologist to use in making a diagnosis. This process of creating additional slides may be time-consuming, not only because it may involve retrieving the block of tissue, cutting it to make a new a slide, and then staining the slide, but also because it may be batched for multiple orders. This may significantly delay the final diagnosis that the pathologist renders. Even after the delay, the new slides still may not have information sufficient to render a diagnosis.

A desire exists for a way to expedite or streamline the slide preparation process, and to ensure that pathology slides have sufficient information to render a diagnosis, by the time the slides are reviewed by a pathologist. Disclosed embodiments ensure that slides may provide information sufficient to render a diagnosis, before a pathologist reviews the slide. The disclosed embodiments may save a pathologist from reviewing slides that provide insufficient information to render a diagnosis.

The foregoing general description and the following detailed description are exemplary and explanatory only and are not restrictive of the disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for determining to order an additional slide based on image analysis of tissue specimens from digital pathology images.

A computer-implemented method for processing an electronic image corresponding to a specimen includes: receiving a target electronic image of a slide corresponding to a target specimen, the target specimen including a tissue sample from a patient; applying a machine learning system to the target electronic image to determine deficiencies associated with the target specimen, the machine learning system having been generated by processing a plurality of training images to predict stain deficiencies and/or predict a needed recut, the training images including images of human tissue and/or images that are algorithmically generated; and based on the deficiencies associated with the target specimen, determining to automatically order an additional slide to be prepared.

In accordance with another embodiment, a system for processing an electronic image corresponding to a specimen includes: at least one memory storing instructions; and at least one processor configured to execute the instructions to perform operations including: receiving a target electronic image of a slide corresponding to a target specimen, the target specimen including a tissue sample from a patient; applying a machine learning system to the target electronic image to determine deficiencies associated with the target specimen, the machine learning system having been generated by processing a plurality of training images to predict stain deficiencies and/or predict a needed recut, the training images including images of human tissue and/or images that are algorithmically generated; and based on the deficiencies associated with the target specimen, determining to automatically order an additional slide to be prepared.

In accordance with another embodiment, a non-transitory computer-readable medium storing instructions that, when executed by processor, cause the processor to perform a method for processing an electronic image corresponding to a specimen, the method including: receiving a target electronic image of a slide corresponding to a target specimen, the target specimen including a tissue sample from a patient; applying a machine learning system to the target electronic image to determine deficiencies associated with the target specimen, the machine learning system having been generated by processing a plurality of training images to predict stain deficiencies and/or predict a needed recut, the training images including images of human tissue and/or images that are algorithmically generated; and based on the deficiencies associated with the target specimen, determining to automatically order an additional slide to be prepared.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 2 is a flowchart illustrating an exemplary method for determining to order additional slides based on image analysis of tissue specimens from digital pathology image(s), using machine learning, according to an exemplary embodiment of the present disclosure.

DESCRIPTION OF THE EMBODIMENTS

Figure 1A:
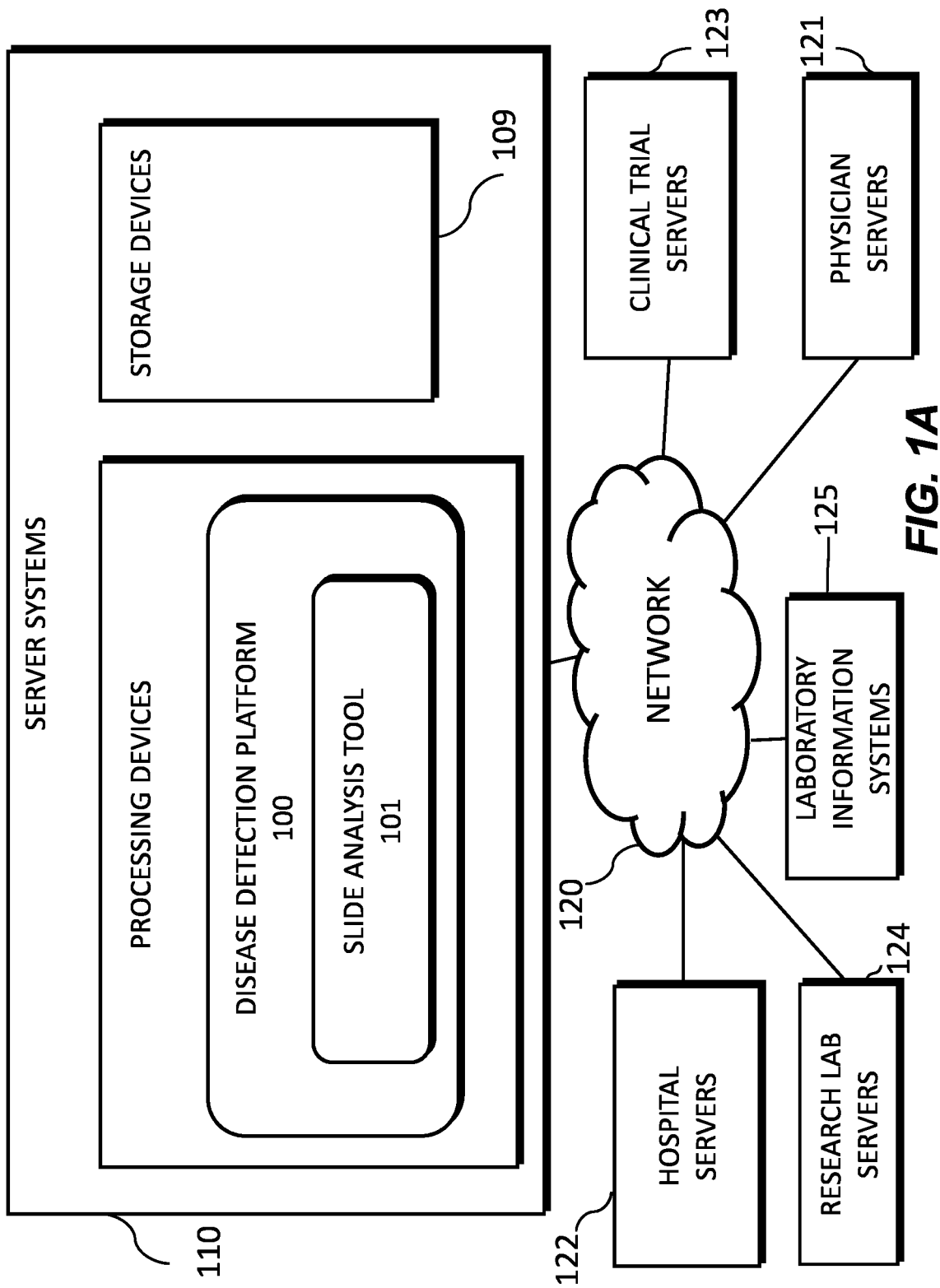
FIG. 1A is an exemplary block diagram of a system and network for determining to order additional slides based on image analysis of tissue specimens from digital pathology image(s), according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Pathology refers to the study of diseases. More specifically, pathology refers to performing tests and analysis that are used to diagnose diseases. For example, tissue samples may be placed onto slides to be viewed under a microscope by a pathologist (e.g., a physician that is an expert at analyzing tissue samples to determine whether any abnormalities exist). That is, pathology specimens may be cut into multiple sections, prepared as slides, and stained for a pathologist to examine and render a diagnosis.

Pathologists may evaluate cancer and other disease pathology slides in isolation. The present disclosure presents a consolidated workflow for improving diagnosis of cancer and other diseases. The workflow may integrate, for example, slide evaluation, tasks, image analysis and cancer detection artificial intelligence (AI), annotations, consultations, and recommendations in one workstation. In particular, the present disclosure describes various exemplary user interfaces available in the workflow, as well as AI tools that may be integrated into the workflow to expedite and improve a pathologist's work.

The process of using computers to assist pathologists is known as computational pathology. Computing methods used for computational pathology may include, but are not limited to, statistical analysis, autonomous or machine learning, and AI. AI may include, but is not limited to, deep learning, neural networks, classifications, clustering, and regression algorithms. By using computational pathology, lives may be saved by helping pathologists improve their diagnostic accuracy, reliability, efficiency, and accessibility. For example, computational pathology may be used to assist with detecting slides suspicious for cancer, thereby allowing pathologists to check and confirm their initial assessments before rendering a final diagnosis.

Histopathology refers to the study of a specimen that has been placed onto a slide. For example, a digital pathology image may be comprised of a digitized image of a microscope slide containing the specimen (e.g., a smear). One method a pathologist may use to analyze an image on a slide is to identify nuclei and classify whether a nucleus is normal (e.g., benign) or abnormal (e.g., malignant). To assist pathologists in identifying and classifying nuclei, histological stains may be used to make cells visible. Many dye-based staining systems have been developed, including periodic acid-Schiff reaction, Masson's trichrome, nissl and methylene blue, and Haemotoxylin and Eosin (H&E). For medical diagnosis, H&E is a widely used dye-based method, with hematoxylin staining cell nuclei blue, eosin staining cytoplasm and extracellular matrix pink, and other tissue regions taking on variations of these colors. In many cases, however, H&E-stained histologic preparations do not provide sufficient information for a pathologist to visually identify biomarkers that may aid diagnosis or guide treatment. In this situation, techniques such as immunohistochemistry (IHC), immunofluorescence, in situ hybridization (ISH), or fluorescence in situ hybridization (FISH), may be used. IHC and immunofluorescence involve, for example, using antibodies that bind to specific antigens in tissues enabling the visual detection of cells expressing specific proteins of interest, which may reveal biomarkers that are not reliably identifiable to trained pathologists based on the analysis of H&E stained slides. ISH and FISH may be employed to assess the number of copies of genes or the abundance of specific RNA molecules, depending on the type of probes employed (e.g. DNA probes for gene copy number and RNA probes for the assessment of RNA expression). If these methods also fail to provide sufficient information to detect some biomarkers, genetic testing of the tissue may be used to confirm if a biomarker is present (e.g., overexpression of a specific protein or gene product in a tumor, amplification of a given gene in a cancer).

A digitized image may be prepared to show a stained microscope slide, which may allow a pathologist to manually view the image on a slide and estimate a number of stained abnormal cells in the image. However, this process may be time consuming and may lead to errors in identifying abnormalities because some abnormalities are difficult to detect.

Computational pathology processes and devices may be used to assist pathologists in detecting abnormalities that may otherwise be difficult to detect. For example, AI may be used to predict biomarkers (such as the over-expression of a protein and/or gene product, amplification, or mutations of specific genes) from salient regions within digital images of tissues stained using H&E and other dye-based methods. The images of the tissues could be whole slide images (WSI), images of tissue cores within microarrays or selected areas of interest within a tissue section. Using staining methods like H&E, these biomarkers may be difficult for humans to visually detect or quantify without the aid of additional testing. Using AI to infer these biomarkers from digital images of tissues has the potential to improve patient care, while also being faster and less expensive.

The detected biomarkers or the image alone could then be used to recommend specific cancer drugs or drug combination therapies to be used to treat a patient, and the AI could identify which drugs or drug combinations are unlikely to be successful by correlating the detected biomarkers with a database of treatment options. This may be used to facilitate the automatic recommendation of immunotherapy drugs to target a patient's specific cancer. Further, this could be used for enabling personalized cancer treatment for specific subsets of patients and/or rarer cancer types.

In the field of pathology today, it may be difficult to provide systematic quality control ("QC"), with respect to pathology specimen preparation, and quality assurance ("QA") with respect to the quality of diagnoses, throughout the histopathology workflow. Systematic quality assurance is difficult because it is resource and time intensive as it may require duplicative efforts by two pathologists. Some methods for quality assurance include (1) second review of first-time diagnosis cancer cases; (2) periodic reviews of discordant or changed diagnoses by a quality assurance committee; and (3) random review of a subset of cases. These are non-exhaustive, mostly retrospective, and manual. With an automated and systematic QC and QA mechanism, quality may be ensured throughout the workflow for every case. Laboratory quality control and digital pathology quality control are critical to the successful intake, process, diagnosis, and archive of patient specimens. Manual and sampled approaches to QC and QA confer substantial benefits. Systematic QC and QA has the potential to provide efficiencies and improve diagnostic quality.

As described above, computational pathology processes and devices of the present disclosure may provide an integrated platform allowing a fully automated process including data ingestion, processing and viewing of digital pathology images via a web-browser or other user interface, while integrating with a laboratory information system (LIS). Further, clinical information may be aggregated using cloud-based data analysis of patient data. The data may come from hospitals, clinics, field researchers, etc., and may be analyzed by machine learning, computer vision, natural language processing, and/or statistical algorithms to do real-time monitoring and forecasting of health patterns at multiple geographic specificity levels.

As described above, example embodiments described herein determine whether enough information has been collected from a tissue specimen to make a diagnosis. For example, computers may be used to analyze an image of a tissue sample to quickly identify whether additional information may be needed about a particular tissue sample, and/or to highlight to a pathologist an area in which he or she should look more closely. When paired with automatic slide segmenting and staining machines, this may provide a fully automated slide preparation pipeline. This automation has, at least, the benefits of (1) minimizing an amount of time wasted by a pathologist determining a slide to be insufficient to make a diagnosis, (2) minimizing the (average total) time from specimen acquisition to diagnosis by avoiding the additional time between when additional tests are ordered and when they are produced, (3) reducing the amount of time per recut and the amount of material wasted by allowing recuts to be done while tissue blocks (e.g., pathology specimens) are in a cutting desk, (4) reducing the amount of tissue material wasted/discarded during slide preparation, (5) reducing the cost of slide preparation by partially or fully automating the procedure, (6) allowing automatic customized cutting and staining of slides that would result in more representative/informative slides from samples, (7) allowing higher volumes of slides to be generated per tissue block, contributing to more informed/precise diagnoses by reducing the overhead of requesting additional testing for a pathologist, and/or (8) identifying or verifying correct properties (e.g., pertaining to a specimen type) of a digital pathology image, etc.

The below embodiments describe various machine learning algorithm training methods and implementations. These embodiments are merely exemplary. Any training methodologies could be used to train a machine learning model and/or system for the specific purpose of enhancing pathology slide preparation and analysis. Below, some exemplary terms are described.

A whole slide image (WSI) may include an entire scanned pathology slide. A training dataset may include a set of whole slide images and/or additional diagnostic data from a set of cases used for training the machine learning (ML) algorithm. A validation dataset may include a set of whole slide images and/or additional diagnostic data from a set of cases used for validating the generalizability of the ML algorithm. A set of labels may be used for each instance in the training data that contain information that an algorithm is being trained to predict (e.g., whether pathologists requested additional testing/re-cuts for a WSI, etc.). A convolutional neural network (CNN) may refer to an architecture that may be built that can scan over the WSI. One embodiment may include training this CNN, using the training labels, to make one prediction per WSI about the likelihood that additional testing/slide preparation is desired. A CNN+Aggregator may refer to an architecture that may be built to incorporate information from a CNN that is executed over multiple localized regions of a WSI. One embodiment may include training this CNN, using the training labels, to make predictions for each region in the WSI about the likelihood that additional testing/slide preparation may be needed due to information in a specimen or scanned region. For additional levels/cuts, the criteria used may be that staining is inadequate/abnormal, only a small volume of tumor is detected (e.g., for prostate if an atypical small acinar proliferation (ASAP) is detected), if an inadequate amount of tissue is present, tissue folds, etc. For rescanning, this may include the presence of bubbles, blur, and/or scanning artifacts, etc. More complex training methodologies, such as Multiple Instance Learning, may be used to overcome issues presented when labels do not match one-to-one with WSI regions. In some embodiments, a second model may take individual predictions over tissue/specimen/image regions as inputs and predict the likelihood that the WSI may need additional testing/slide preparation. Model Uncertainty may refer to a machine learning model that may be trained to predict any parameter about, or related to, a WSI, e.g., detection of a presence of cancer or other diseases. The level of uncertainty the machine learning model has about specific predictions could be computed using a variety of methods, e.g., identifying an ambiguous range of the probability values such as those close to the threshold, using out-of-distribution techniques (Out-of-Distribution detector for Neural Networks (ODIN), tempered mix-up, Mahalanobis distance on the embedding space), etc. This uncertainty could be used to estimate the likelihood a slide may need additional testing/preparation.

According to one embodiment, a machine learning model could be trained to predict a characteristic about a WSI that is usually a proxy for the need to do additional testing, e.g., presence of high-grade prostatic intraepithelial neoplasia (HGPIN) or ASAPs, etc. The output from this model could then be fed into a model to estimate the likelihood that a slide may need additional testing/preparation.

The above methods may be implemented using additional data regarding a specific WSI. For example, according to one embodiment, additional data may include one or more of (a) patient data such as genomic testing, family history, previous medical history, etc.; and/or (b) procedure data such as physician notes/recommendation, observations from lab technicians, etc.

Exemplary global outputs of the disclosed embodiments may contain information or slide parameter(s) about an entire slide, e.g., the depicted specimen type, the overall quality of the cut of the specimen of the slide, the overall quality of the glass pathology slide itself, or tissue morphology characteristics. Exemplary local outputs may indicate information in specific regions of a slide, e.g., a particular slide region may be labeled as blurred or containing an irrelevant specimen. The present disclosure includes embodiments for both developing and using the disclosed slide preparation automation, as described in further detail below.

FIG. 1A illustrates a block diagram of a system and network for determining to order additional slides based on image analysis of tissue specimens from digital pathology image(s), using machine learning, according to an exemplary embodiment of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present application, the electronic network 120 may also be connected to server systems 110, which may include processing devices that are configured to implement a disease detection platform 100, which includes a slide analysis tool 101 for determining specimen property or image property information pertaining to digital pathology image(s), and using machine learning to determine to order an additional slide, according to an exemplary embodiment of the present disclosure.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities. For example, the processing devices may include a machine learning tool for a disease detection platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in a LIS 125.

Figure 1B:
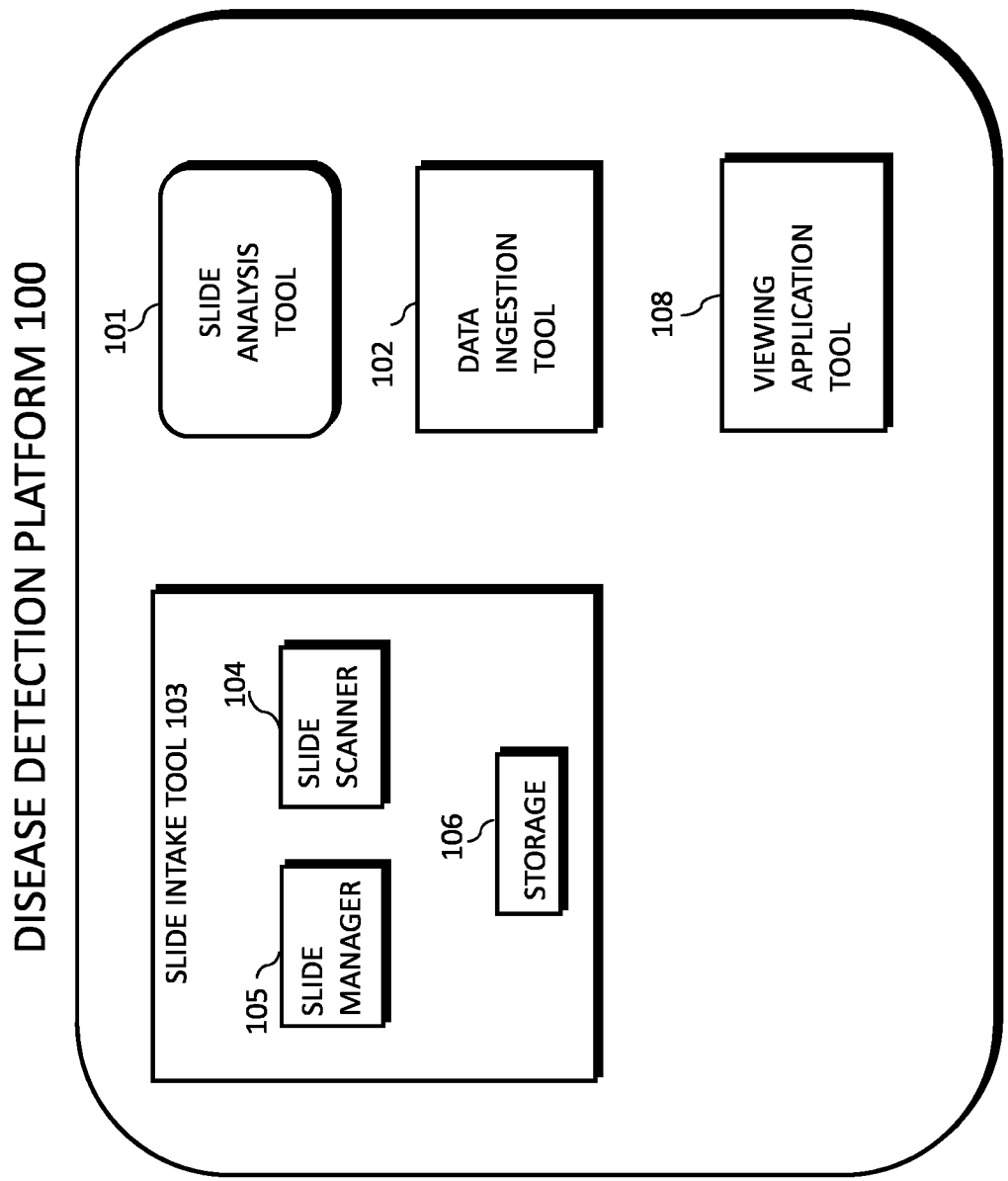
FIG. 1B is an exemplary block diagram of a disease detection platform 100, according to an exemplary embodiment of the present disclosure.

FIG. 1B illustrates an exemplary block diagram of a disease detection platform 100 for determining to order additional slides based on image analysis of tissue specimens from digital pathology image(s), using machine learning, according to an exemplary embodiment of the present disclosure.

Specifically, FIG. 1B depicts components of the disease detection platform 100, according to one embodiment. For example, the disease detection platform 100 may include a slide analysis tool 101, a data ingestion tool 102, a slide intake tool 103, a slide scanner 104, a slide manager 105, a storage 106, and a viewing application tool 108.

The slide analysis tool 101, as described below, refers to a process and system for determining to order additional slides based on image analysis of tissue specimens from digital pathology image(s), using machine learning, according to an exemplary embodiment of the present disclosure.

The data ingestion tool 102 refers to a process and system for facilitating a transfer of the digital pathology images to the various tools, modules, components, and devices that are used for determining to order additional slides based on image analysis of tissue specimens from digital pathology image(s), according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., pathologist) with specimen property or image property information pertaining to digital pathology image(s), according to an exemplary embodiment. The information may be provided through various output interfaces (e.g., a screen, a monitor, a storage device, and/or a web browser, etc.).

The slide analysis tool 101, and each of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the slide analysis tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools, and modules may be located on a device that may be connected to an electronic network 120, such as the Internet or a cloud service provider, through one or more computers, servers, and/or handheld mobile devices.

Figure 1C:
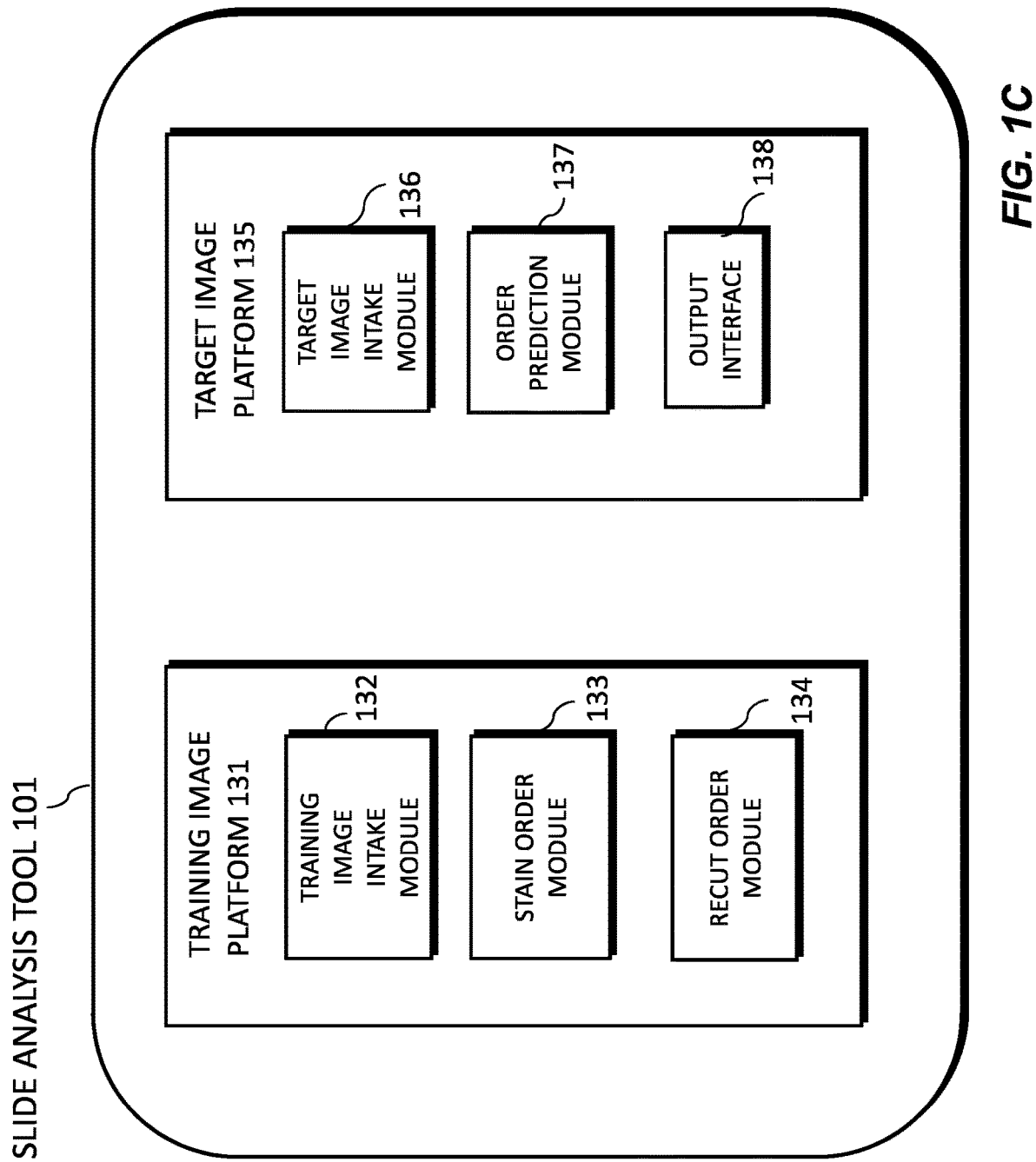
FIG. 1C is an exemplary block diagram of a slide analysis platform 101, according to an exemplary embodiment of the present disclosure.

FIG. 1C illustrates an exemplary block diagram of a slide analysis tool 101, according to an exemplary embodiment of the present disclosure. The slide analysis tool 101 may include a training image platform 131 and/or a target image platform 135.

According to one embodiment, the training image platform 131 may include a training image intake module 132, a stain module 133, and/or a recut module 134.

The training image platform 131, according to one embodiment, may create or receive training images that are used to train a machine learning model to effectively process, analyze, and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized tissue samples from a 3D imaging device, such as microCT.

The training image intake module 132 may create or receive a dataset comprising one or more training images corresponding to either or both of images of a human tissue and images that are graphically rendered. For example, the training images may be received from any one or any combination of the server systems 110, physician servers 121, hospital servers 122, clinical trial servers 123, research lab servers 124, and/or laboratory information systems 125. This dataset may be kept on a digital storage device. The stain module 133 may predict which new stains should be ordered for a selected slide due to a deficiency, based on the received digital image(s) and received data. The recut module 134 may predict whether a recut will be needed, based on the received digital image(s) and received data.

According to one embodiment, the target image platform 135 may include a target image intake module 136, a deficiency prediction module 137, and an output interface 138. The target image platform 135 may receive a target image and apply the machine learning model to the received target image to determine to order an additional slide. For example, the target image may be received from any one or any combination of the server systems 110, physician servers 121, hospital servers 122, clinical trial servers 123, research lab servers 124, and/or laboratory information systems 125. The target image intake module 136 may receive a target image corresponding to a target specimen. The deficiency prediction module 137 may apply the machine learning model to the target image to stain deficiencies and/or predict a needed recut associated with the target specimen.

The output interface 138 may be used to output information about the target image and the target specimen. (e.g., to a screen, monitor, storage device, web browser, etc.).

FIG. 2 is a flowchart illustrating an exemplary method of a tool for determining to order additional slides based on image analysis of tissue specimens from digital pathology image(s), according to an exemplary embodiment of the present disclosure. For example, an exemplary method 200 (e.g., steps 202 to 206) may be performed by the slide analysis tool 101 automatically or in response to a request from a user (e.g., physician, pathologist, etc.).

According to one embodiment, the exemplary method 200 for determining to order additional slides may include one or more of the following steps. In step 202, the method may include receiving a target image of a slide corresponding to a target specimen, the target specimen comprising a tissue sample from a patient. For example, the target image may be received from any one or any combination of the server systems 110, physician servers 121, hospital servers 122, clinical trial servers 123, research lab servers 124, and/or laboratory information systems 125.

In step 204, the method may include applying a machine learning model to the target image to predict pathologist order information associated with the target specimen. The predicting the pathologist order information may include determining a likelihood that the additional slide is to be prepared based on specimen information of the target specimen, and determining, in response to the likelihood being greater than or equal than a predetermined amount, to automatically order the additional slide to be prepared.

The machine learning model may be generated by processing a plurality of training images to predict stain order information and/or recut order information, and the training images may include images of human tissue and/or images that are algorithmically generated. The machine learning model may be implemented using machine learning methods for classification and regression. Training inputs could include real or synthetic imagery. Training inputs may or may not be augmented (e.g., adding noise). Exemplary machine learning models may include, but are not limited to, any one or any combination of Neural Networks, Convolutional neural networks, Random Forest, Logistic Regression, and Nearest Neighbor. Convolutional neural networks and other neural network variants may learn directly from pixels to learn features that generalize well, but they typically require large amounts of training data. The alternative exemplary models typically operate on features from a convolutional network or using hand-engineered computer vision feature extraction techniques (e.g., SIFT, SURF, etc.), which often work less effectively if large amounts of data are available. The training images may be received from any one or any combination of the server systems 110, physician servers 121, hospital servers 122, clinical trial servers 123, research lab servers 124, and/or laboratory information systems 125. This dataset may be kept on a digital storage device. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, IHC, molecular pathology, etc.; and/or (b) digitized tissue samples from a 3D imaging device, such as microCT.

In step 206, the method may include, based on the predicted pathologist order information associated with the target specimen, determining to automatically order an additional slide to be prepared. The additional slide may be automatically ordered in response to the machine learning model identifying a diagnosis that automatically initiates an additional test. This diagnosis may be any one or any combination of lung adenocarcinoma, breast carcinoma, endometrioid adenocarcinoma, colonic adenocarcinoma, amyloid presence, and/or fungal organisms. The additional slide may be automatically ordered in response to the machine learning model identifying a morphology that automatically triggers a genetic test. The morphology may be at least one of BAP1 deficient nevi and/or succinate dehydrogenase deficient tumors. Ordering the additional slide may include ordering a new stain to be prepared for the slide corresponding to the target specimen and/or ordering a recut for the slide corresponding to the target specimen. The method may further include outputting an alert on a display indicating that the additional slide is being prepared.

Figure 3:
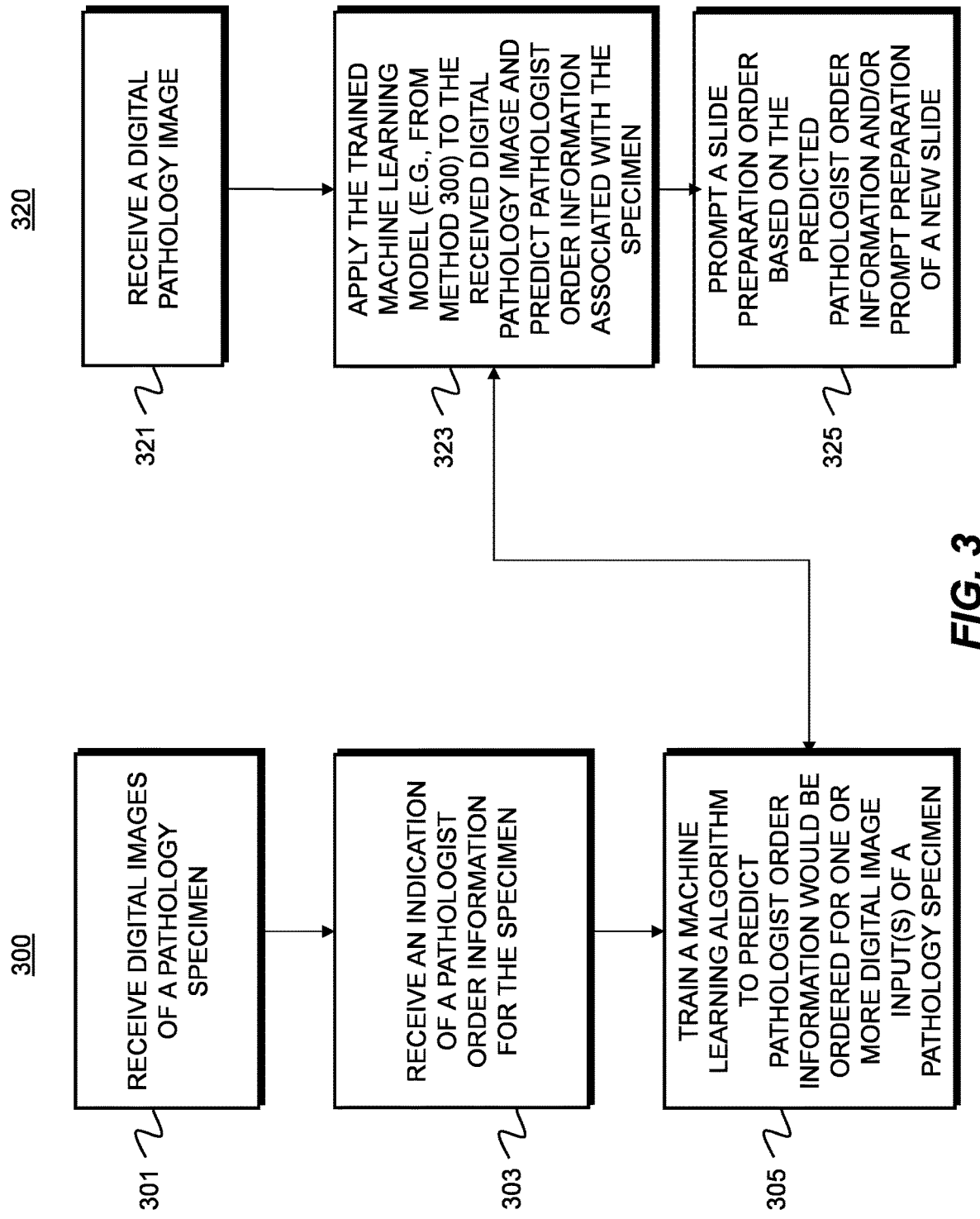
FIG. 3 is a flowchart of an exemplary method for determining slide preparation parameters, according to an exemplary embodiment of the present disclosure.

As illustrated in FIG. 3, according to one embodiment, exemplary methods 300 and 320 for determining slide preparation parameter(s) may include one or more of the steps below. In step 301, during a training phase, the method may include receiving a digital image of a pathology specimen (e.g., histology, cytology, etc.) in a digital storage device (e.g., hard drive, network drive, cloud storage, RAM, etc.). The received image may be 2D (e.g., histology slides or unstained tissue cuts) or 3D (e.g., micro CT, reconstructed 2D histology, etc.).

According to one embodiment, in step 303, the method may include receiving an indication of whether a pathologist ordered new information for the specimen shown in the digital image. This step may include receiving order information that a pathologist or other medical professional associated with, or entered, for the specimen. New order information might include additional stains, additional cuts, genomic testing, genetic testing, in-vitro lab tests, radiology imaging, computational (e.g., artificial intelligence) diagnostic tests, etc.

In step 305, the method may include training a machine learning algorithm to predict whether and/or what order information may be associated with one or more input/new digital images. This algorithm may be implemented in multiple ways. For example, according to one embodiment, the algorithm may be implemented by any one or any combination of (1) machine learning algorithms and/or architectures, such as neural network methods, e.g., convolutional neural networks (CNNs) and recurrent neural networks (RNNs); (2) training methodologies, such as Multiple Instance Learning, Reinforcement Learning, Active Learning, etc.; (3) attribute/feature extraction including but not limited to any one or any combination of estimated percentage of tissue in slide, base statistics on RGB, HSV or other color-space, and presence of slide preparation issues or imaging artifacts such as bubbles, tissue folds, abnormal staining, etc.; (4) using measure(s) of uncertainty in the model predictions over other metrics as a proxy for needing additional information; and (5) the output or associated metrics from models trained on a different task.

According to one or more embodiments, any of the above algorithms, architectures, methodologies, attributes, and/or features may be combined with any or all of the other algorithms, architectures, methodologies, attributes, and/or features. For example, any of the machine learning algorithms and/or architectures (e.g., neural network methods, convolutional neural networks (CNNs), recurrent neural networks (RNNs), etc.) may be trained with any of the training methodologies (e.g., Multiple Instance Learning, Reinforcement Learning, Active Learning, etc.)

The description of the terms below is merely exemplary and is not intended to limit the terms in any way.

A label may refer to information about an input to a machine learning algorithm that the algorithm is attempting to predict.

For a given image of size N×M, a segmentation may be another image of size N×M that, for each pixel in an original image, assigns a number that describes the class or type of that pixel. For example, in a WSI, elements in the mask may categorize each pixel in the input image as belonging to the classes of, e.g., background, tissue and/or unknown.

Slide level information may refer to information about a slide in general, but not necessarily a specific location of that information in the slide.

A heuristic may refer to a logic rule or function that deterministically produces an output, given inputs. For example: if a prediction that a slide should be rescanned is greater than or equal to 32%, then output one, if not, output 0. Another example heuristic may be that if beyond a predetermined percentage or portion of a slide is classified as unknown, then flag for re-scanning.

Embedding may refer to a conceptual high-dimensional numerical representation of low-dimensional data. For example, if a WSI is passed through a CNN training to classify tissue type, the numbers on the last layer of the network may provide an array of numbers (e.g., in the order of thousands) that contain information about the slide (e.g., information about a type of tissue).

Slide level prediction may refer to a concrete prediction about a slide as a whole. For example, a slide level prediction may be that the slide has a scanning issue, bubbles, tissue folds, etc. Further, slide level prediction may refer to individual probability predictions over a set of defined classes (e.g., 33% chance of bubbles, 1% chance of tissue folds, 99% chance of scanning artifacts, etc.).

A classifier may refer to a model that is trained to take input data and associate it with a category.

According to one or more embodiments, the machine learning model may be trained in different ways. For example, the training of the machine learning model may be performed by any one or any combination of supervised training, semi-supervised training, unsupervised training classifier training, mixed training, and/or uncertainty estimation. The type of training used may depend on an amount of data, a type of data, and/or a quality of data. Table 1 below describes a non-limiting list of some types of training and the corresponding features.

TABLE 1

| Index | Input | Label | Model | Output |
|---|---|---|---|---|
| 1 | WSI Embedding | Segmentation | CNN, RNN, MLP | Predicted Segmentation Embedding |
| 2 | WSI Embedding | Slide Level Information | CNN, RNN, MLP | Embedding Slide level prediction |

TABLE 1-continued

| Index | Input | Label | Model | Output |
|---|---|---|---|---|
| 3 | WSI Embedding | — | CNN, RNN, MLP | Embedding |
| 4 | Embedding | Slide Level Information | SVM, MLP, RNN, Random Forests | Slide level prediction |
| 5 | Slide level prediction | Measure of how wrong the prediction was | MLP, RNN, Statistical Model | Predict a likelihood that an original prediction is wrong |

Supervised training may be used with a small amount of data to provide a seed for a machine learning model. In supervised training, the machine learning model may look for a specific item (e.g., bubbles, tissue folds, etc.), flag the slide, and quantify how much of the specific item is present in the slide.

According to one embodiment, an example fully supervised training may take as an input a WSI and may include a label of segmentation. Pipelines for a fully supervised training may include (1) 1; (2) 1, Heuristic; (3) 1, 4, Heuristic; (4) 1, 4, 5, Heuristic; and/or (5) 1, 5, Heuristic. Advantages of a fully supervised training may be that (1) it may require fewer slides and/or (2) the output is explainable because (a) it may be known which areas of the image contributed to the diagnosis; and (b) it may be known why a slide is rejected (e.g., bubbles found, tissue fold found, etc.). A disadvantage of using a fully supervised training may be that it may require large amounts of segmentation which may be difficult to acquire.

According to one embodiment, an example semi-supervised (e.g., weakly supervised) training may take as an input WSI and may include a label of slide level information. Pipelines for a semi-supervised training may include (1) 2; (2) 2, Heuristic; (3) 2, 4, Heuristic; (4) 2, 4, 5, Heuristic; and/or (5) 2, 5, Heuristic. Advantages of using a semi-supervised training may be that (1) the types of labels required may be present in many hospital records; and (2) output is explainable because (a) it may be known which areas of the image contributed most to the diagnosis; and (b) it may be known why a slide was rejected (e.g., bubbles found, tissue fold found, etc.). A disadvantage of using a semi-supervised training is that it may be difficult to train. For example, the model may need to use a training scheme such as Multiple Instance Learning, Activate Learning, and/or distributed training to account for the fact that there is limited information about where in the slide the information is that should lead to a decision.

According to one embodiment, an example unsupervised training may take as an input a WSI and may require no label. The pipelines for an unsupervised training may include (1) 3, 4; and/or (2) 3, 4, Heuristic. An advantage of unsupervised training may be that it does not require any labels. Disadvantages of using an unsupervised training may be that (1) it may be difficult to train. For example, it may need to use a training scheme such as Multiple Instance Learning, Activate Learning, and/or distributed training to account for the fact that there is limited information about where in the slide the information is that should lead to a decision; (2) it may require additional slides; and/or (3) it may be less explainable because it might output a prediction and probability without explaining why that prediction was made.

According to one embodiment, an example mixed training may include training any of the example pipelines described above for fully supervised training, semi-supervised training, and/or unsupervised training, and then use the resulting model as an initial point for any of the training methods. Advantages of mixed training may be that (1) it may require less data; (2) it may have improved performance; and/or (3) it may allow a mixture of different levels of labels (e.g., segmentation, slide level information, no information). Disadvantages of mixed training may be that (1) it may be more complicated and/or expensive to train; and/or (2) it may require more code that may increase a number and complexity of potential bugs.

According to one embodiment, an example uncertainty estimation may include training any of the example pipelines described above for fully supervised training, semi-supervised training, and/or unsupervised training, for any task related to slide data using uncertainty estimation in the end of the pipeline. Further, a heuristic or classifier may be used to predict whether a recut should be performed based on an amount of uncertainty in the prediction of the test. An advantage of uncertainty estimation may be that it is robust to out-of-distribution data. For example, when unfamiliar data is presented, it may still correctly predict that it is uncertain. Disadvantages of uncertainty estimation may be that (1) it may need more data; (2) it may have poor overall performance; and/or (3) it may be less explainable because the model might not necessarily identify how a slide or slide embedding is abnormal.

According to one embodiment, an ensembles training may include simultaneously running models produced by any of the example pipelines described above, and combining the outputs by a heuristic or a classifier to produce robust and accurate results. Advantages of ensembles training may be that (1) it is robust to out-of-distribution data; and/or (2) it may combine advantages and disadvantages of other models, resulting in a minimization of disadvantages (e.g., a supervised training model combined with an uncertainty estimation model, and a heuristic that uses a supervised model when incoming data is in distribution and uses an uncertainty model when data is out of distribution, etc.). Disadvantages of ensembles training may be that (1) it may be more complex; and/or (2) it may be expensive to train and run.

Training techniques discussed herein may also proceed in stages, where images with greater annotations are initially used for training, which may allow for more effective later training using slides that have fewer annotations, are less supervised, etc.

Training may begin using the slides that are the most thoroughly annotated, relative to all the training slide images that may be used. For example, training may begin using supervised learning. A first set of slides images may be received or determined with associated annotations. Each slide may have marked and/or masked regions and may include information such as whether the slide should be rejected. The first set of slides may be provided to a training algorithm, for example a CNN, which may determine correlations between the first set of slides and their associated annotations.

After training with the first set of images is completed, a second set of slide images may be received or determined having fewer annotations than the first set, for example with partial annotations. In one embodiment, the annotations might only indicate that the slide has a diagnosis or quality issue associated with it, but might not specify what or where disease may be found, etc. The second set of slide images may be trained using a different training algorithm than the first, for example Multiple Instance Learning. The first set of training data may be used to partially train the system, and may make the second training round more effective at producing an accurate algorithm.

In this way, training may proceed in any number of stages, using any number of algorithms, based on the quality and types of the training slide images. These techniques may be utilized in a situations where multiple training sets of images are received, which may be of varying quality, annotation levels, and/or annotation types.

According to one embodiment, an exemplary method 320 for using the tool may include one or more of the steps below. In step 321, the method may include receiving a digital image of a pathology specimen (e.g., histology, cytology, etc.) in a digital storage device (e.g., hard drive, network drive, cloud storage, RAM, etc.). In step 323, the method may include applying the algorithm from the training procedure (e.g., method 300) to predict the likelihood that the digital image provides insufficient information for a diagnosis and/or the likelihood that the digital image may be associated with order information for an improved pathology slide to be made. This prediction may be performed at the level of a specimen, a slide, a tissue block, etc.

In step 325, the method may include predicting order information associated with the received digital image. The order information may include a type of testing or slide parameter(s) to order. Testing may include additional stains, additional cuts, genomic testing, genetic testing, in-vitro lab tests, radiology imaging, computational (e.g., artificial intelligence) diagnostic tests, etc. This prediction may be output to an electronic storage device. In one embodiment, the predicted likelihood may be used to automatically trigger an order for new information from a histology technician. The predicted likelihood or predicted order information may be used to prompt an automatic preparation pipeline to prepare one or more additional slides (e.g., re-cuts, staining, etc.). The automatic trigger or slide preparation may be performed by a heuristic or auxiliary system. Alternately or in addition, step 325 may include generating a visual indicator to alert a user (e.g., a pathologist, histology technician, etc.) that new information on a slide may be desired to make a diagnosis. A user may then order new information, based on the alert. The alert may allow a user to initiate preparation for a new slide earlier, rather than later.

Techniques discussed herein provide a heuristic for determining whether to produce a stain, and a method for streamlining pathology slide analysis. One aspect of streamlining slide analysis includes ordering new slide(s) and/or automating slide order information. The slide order machine learning embodiments described above present solution(s) for this aspect. Another aspect of streamlining pathology slide analysis may include minimizing an expected cost of running additional tests/generating additional specimen slides. According to one embodiment, minimizing the cost may follow the function below:

$$\min((A+B)*FN(th)+C*FP(th)), \text{ where}$$

A: Average cost of a delayed diagnosis;
B: Average cost for a pathologist to decide additional staining is required;
C: Cost of additional test;
FN(th): False negative rate across the validation set as a function of threshold; and
FP(th): False positive rate in across the validation set as a function of threshold.

The above-described training and usage phases may include embodiments usable in research and/or production/clinical/industrial settings. These are described in detail below.

According to one embodiment, a method may include predicting when a new stain is ordered by a pathologist. For example, when a pathologist is struggling with a diagnosis or finds specific borderline signs of cancer, the pathologist may request for a slide to be prepared with an additional stain, e.g., immunohistochemistry (IHC), molecular pathology, Congo Red, etc.

Figure 4:
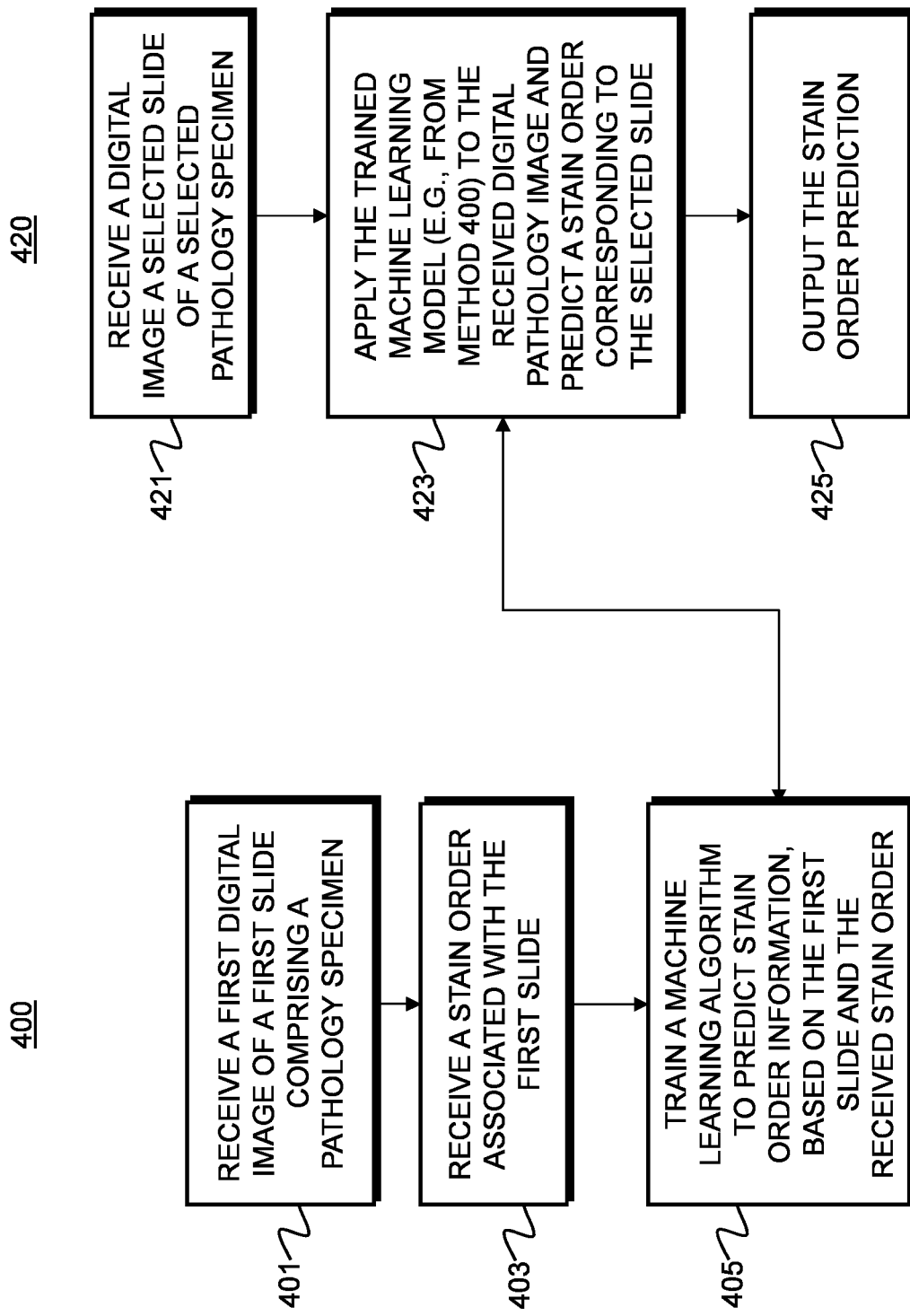
FIG. 4 is a flowchart of an exemplary method of generating and using a stain order prediction tool, according to an exemplary embodiment of the present disclosure.

According to one embodiment illustrated in FIG. 4, an exemplary method 400 for developing a stain order prediction tool may include one or more of the steps below. In step 401, the method may include receiving a first digital image of a first slide comprising a pathology specimen (e.g., histology, cytology, etc.) in a digital storage device (e.g., hard drive, network drive, cloud storage, RAM, etc.). In step 403, the method may include receiving, for the first slide, an indication of whether a pathologist ordered a new stain for that slide. This step may include receiving a stain order associated with the first slide. For example, the indication for the slide may state the exact stain that was ordered. Additional information about the specimen of the slide may also be received, e.g., data on the tissue type from with the specimen was taken and/or any diagnostic data associated with the patient or case associated with the specimen.

In step 405, the method may include training a machine learning algorithm to receive a second digital image of a pathology specimen and receive data (e.g., slide order information) associated with the second digital image. A trained machine learning algorithm may then predict whether a new stain was ordered for a selected slide, based on the received digital image(s) and received data (e.g., step 405). The trained machine learning algorithm may also predict which (new) stains were ordered for a selected slide, based on the received digital image(s) and received data (e.g., step 405). This algorithm may be implemented in multiple ways by using any combination of (1) Neural networks such as CNNs, RNNs, etc.; (2) Training methodologies, such as Multiple Instance Learning, Reinforcement Learning, Active Learning, etc.; (3) Feature extraction including but not limited to any one or any combination of percentage of tissue in slide, base statistics on RGB, HSV or other colorspaces, a presence of slide preparation or imaging artifacts such as bubbles, tissue folds, abnormal staining, etc.; and (4) simple classification methods, such as random forest, support vector machine (SVM), multiplayer perceptron (MLP), etc. The above description of machine learning algorithms for FIG. 3 (e.g., Table 1 and corresponding description) may also apply to the machine learning algorithms of FIG. 4.

An exemplary method 420 for using the disclosed stain order prediction tool may include one or more of the steps below. In step 421, the method may include receiving one or more digital images of a slide of a pathology specimen (e.g., histology, cytology, etc.) in a digital storage device (e.g., hard drive, network drive, cloud storage, RAM, etc.) (e.g., step 421). Information about the specimen may be received, e.g., a tissue type from which the specimen harvested and/or any diagnostic data associated with the selected patient or selected case. In step 423, the method may include predicting, using the trained machine learning algorithm (e.g., of method 400) the likelihood that a new stain is desired for the slide. Step 423 may also include predicting a stain order for the slide.

In step 425, the method may include outputting the prediction to an electronic storage device. The predicted likelihood or predicted stain order may be used to automatically trigger an order for a histology technician. In one embodiment, a visual indicator may be generated to alert a user (e.g., a pathologist, histology technician, etc.) that a new stain may be desired, so that the user may promptly order the new stain. Alternately, or in addition, the predicted likelihood or predicted stain order may be used as part of an automated slide staining pipeline to prepare one or more slides with the required stain. Example methods include, but are not limited to, low model information, predicting high risk lesions, identifying diagnoses that may automatically need additional tests, and identifying suspicious morphology that automatically triggers genetic testing.

Examples of diagnoses that may automatically need additional tests may include any one or any combination of (1) Lung adenocarcinoma triggers a panel of immunostains and recuts for molecular testing (e.g., EGFR (Epidermal Growth Factor Receptor), KRAS (Kirsten RAt Sarcoma), ALK (anaplastic lymphoma receptor tyrosine kinase), ROS, BRAF (B-Raf proto-oncogene), MET (MET Proto-Oncogene, Receptor Tyrosine Kinase), etc.); (2) Breast carcinoma triggers a hormone receptor immunostain panel (e.g., ER (oestrogen receptor), PR (progesterone receptor)<Her2 (human epidermal growth factor receptor type 2)); (3) Endometrioid adenocarcinoma and colonic adenocarcinoma trigger mismatch repair immunostains (e.g., MLH1, MSH2, PMS2, MSH6 genes; (4) Amyloid presence triggers Congo Red; and (5) Fungal organisms trigger, e.g., PAS (Periodic acid—Schiff) and GMS (Grocott methenamine silver).

Examples of suspicious morphology that automatically trigger genetic testing may include (1) BAP1 deficient nevi, triggers BAP1 immunostain; and/or (2) succinate dehydrogenase deficient tumors triggers SDH (succinate dehydrogenase) immunostain.

According to one embodiment, some diagnoses and/or stain order predictions may prompt at least one additional stain that may be triggered automatically, e.g., if the algorithm of method 420 has determined a diagnosis within a threshold or certainty and/or determined one set of stain order information. Additionally, some features of the pathology images may be subtle and additional stains may assist the pathologist to determine a diagnosis. In one embodiment, the additional stain(s) may be prompted/ordered once the algorithm of method 420 detects that an image enhancement or improved slide is desired.

According to one embodiment, examples of situations in which at least one additional stain may be triggered automatically may include diagnoses that trigger one or more immunostains. For example, lung adenocarcinoma may trigger a panel of immunostains and recuts for molecular testing (EGFR, KRAS, ALK, ROS, BRAF, MET, etc.). Additionally, breast carcinoma may trigger a hormone receptor immunostain panel (ER, PR<Her2). Also, endometrioid adenocarcinoma and colonic adenocarcinoma may trigger mismatch repair immunostains (MLH1, MSH2, PMS2, MSH6).

According to one embodiment, a pathology image may include certain features that are subtle and difficult to detect. In this case, an automatic ordering of more stains may be triggered to enhance some features to assist a pathologist in determining a diagnosis. For example, a BAP1 deficient nevi detected by the algorithm may predict tumor predisposition, and a BAP1 immunostain may be ordered. As another example, if a succinate dehydrogenase deficient tumor is recognized, an SDH immunostain may be ordered. As another example, if amyloid is detected, a Congo red stain may be ordered to highlight the amyloid. As another example, if fungal organisms are detected by the algorithm, a Periodic acid—Schiff (PAS) and/or Gomori's methenamine silver (GMS) stain may be ordered to highlight the fungal organisms.

According to one embodiment, a method may include predicting when a recut is to be ordered by a pathologist. For example, when a pathologist detects a possible border of cancer in a slide, or when a pathologist detects that a slide does not capture enough of a specimen's cross section to render a diagnosis, the pathologist may request for an additional cut to be made from the specimen, and a new slide to be prepared.

Figure 5:
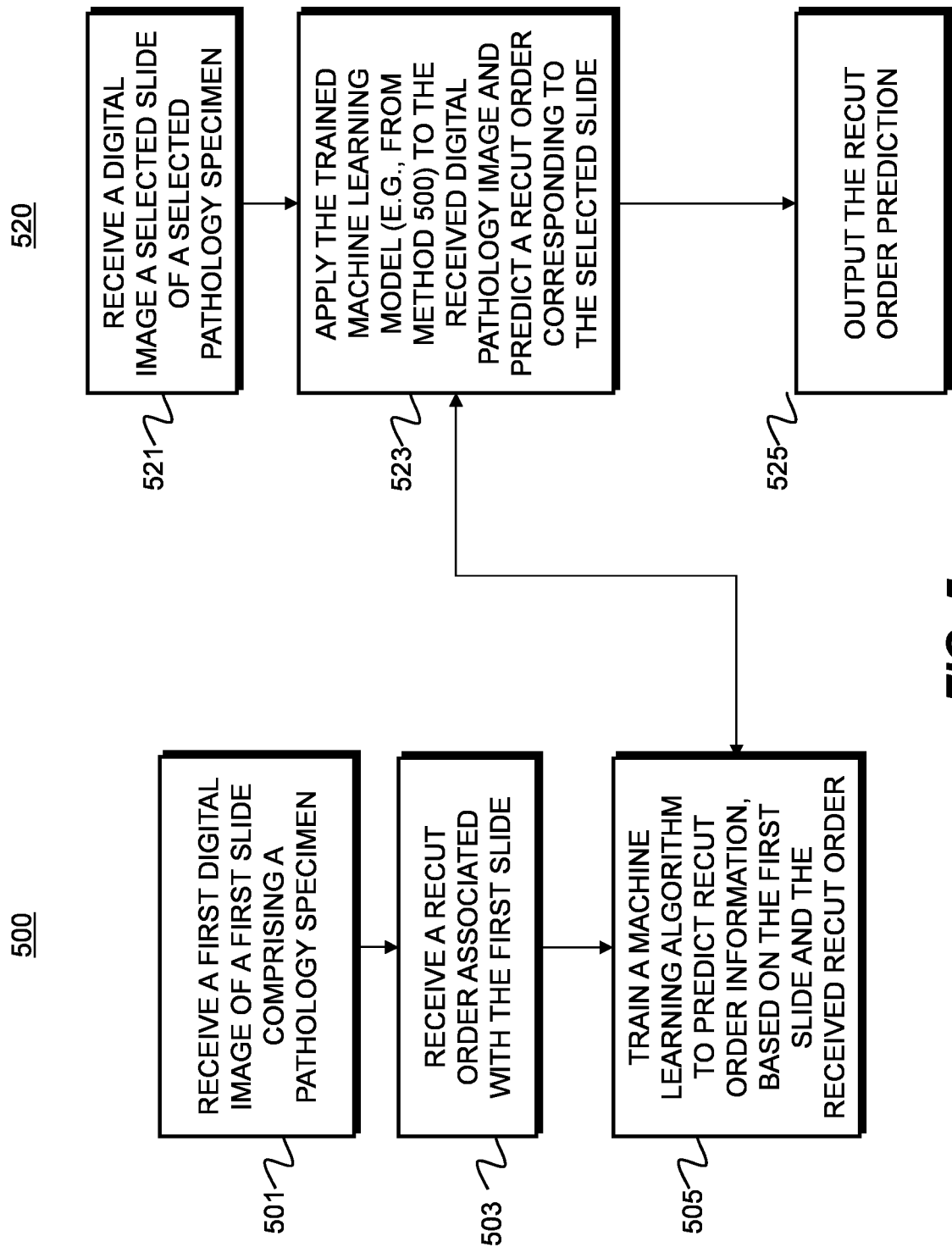
FIG. 5 is a flowchart of an exemplary method of generating and using a recut order prediction tool, according to an exemplary embodiment of the present disclosure.

According to one embodiment illustrated in FIG. 5, an exemplary method 500 for developing a recut order prediction tool may include one or more of the steps below. In step 501, the method may include receiving a digital image of a first slide comprising a pathology specimen (e.g., histology, cytology, etc.) in a digital storage device (e.g., hard drive, network drive, cloud storage, RAM, etc.). In step 503, the method may include receiving an indication for a tissue block of the specimen, of whether the pathologist ordered a recut for that tissue block. This step may include receiving a recut location of the tissue block, associated with the first slide. For example, the indication for each block could state exactly where the recut was ordered (e.g., above or below each slide in the block). Additional information about the specimen may also be received, e.g., data on the tissue type from with the specimen was taken and/or any diagnostic data associated with the patient or case associated with the specimen. Other examples of additional information may include information about the gross description of the specimen (e.g., images of the gross specimen, test description, size and shape dimensions, etc.).

According to one embodiment, in step 505, the method may include training a machine learning algorithm to predict whether a recut was ordered for an input slide, based on received digital images of pathology specimen(s) and additional information corresponding to each digital image/pathology specimen. For example, the resultant trained machine learning algorithm may predict whether a recut was ordered for each tissue block and/or predict a location of the recut (e.g., above or below the cut of an input slide associated with the tissue block). This algorithm could be implemented in multiple ways by using any combination of (1) neural networks such as CNNs, recurrent neural networks (RNNs), etc.; (2) training methodologies such as Multiple Instance Learning, Reinforcement Learning, Active Learning, etc.; (3) feature extraction including but not limited to (a) percentage of tissue in slide, (b) base statistics on RGB (red, green, blue), HSV (hue, saturation, value), HSL (hue, saturation, lightness), or other color-spaces, and (c) a presence of slide preparation or imaging artifacts such as bubbles, tissue folds, abnormal staining, etc.; and/or (4) simple classification methods such as random forest, SVM, MLP, etc.

An exemplary method 520 for developing a recut order prediction tool may include one or more of the steps below. In step 521, the method may include receiving one or more digital images of a slide of a pathology specimen (e.g., histology, cytology, etc.) in a digital storage device (e.g., hard drive, network drive, cloud storage, RAM, etc.). Information about the specimen may be received, e.g., a tissue type from which the specimen harvested and/or any diagnostic data associated with the selected patient or selected case. In step 523, the method may include predicting, using the trained machine learning algorithm (e.g., of method 500), the likelihood that a recut is desired for a tissue block associated with the specimen. Step 523 may also include predicting a recut order (e.g., recut location) for the slide.

According to one embodiment, in step 525, the method may include outputting the prediction to an electronic storage device (e.g., step 525). The predicted likelihood or predicted recut order may be used to automatically trigger an order for a histology technician. In one embodiment, a visual indicator may be generated to alert a user (e.g., a pathologist, histology technician, etc.) that a new stain may be desired, so that the user may promptly order the new stain. In one embodiment, an output may include prompting an automatic slide segmenting machine to cut one or more additional slides from the tissue block associated with the specimen. An output may further include a determination of the recut location (e.g., how deep into the tissue to cut) and/or the axis for the next recut order. In one embodiment, an additional system may be used to compute precise parameters for generating the recut (e.g., recut location, axis, etc.). Some example methods for determining or computing recut order information may include, but are not limited to (1) from the past N cuts, estimate the amount of tissue to be present in a slide as a function of the location from where a prior specimen was cut and maximize said function to predict the next best location to cut; (2) if small/ambiguous signs of pathogens or cancer are detected, order a recut close (e.g., within a predetermined distance/distance threshold) to the first location/depth to increase the amount of information collected about that suspicious region until ambiguity is resolved; and/or (3) if grading is ambiguous, order a recut close (e.g., within a predetermined distance/distance threshold) to the first location/depth to increase the amount of information collected about that suspicious region until ambiguity is resolved.

Figure 6:
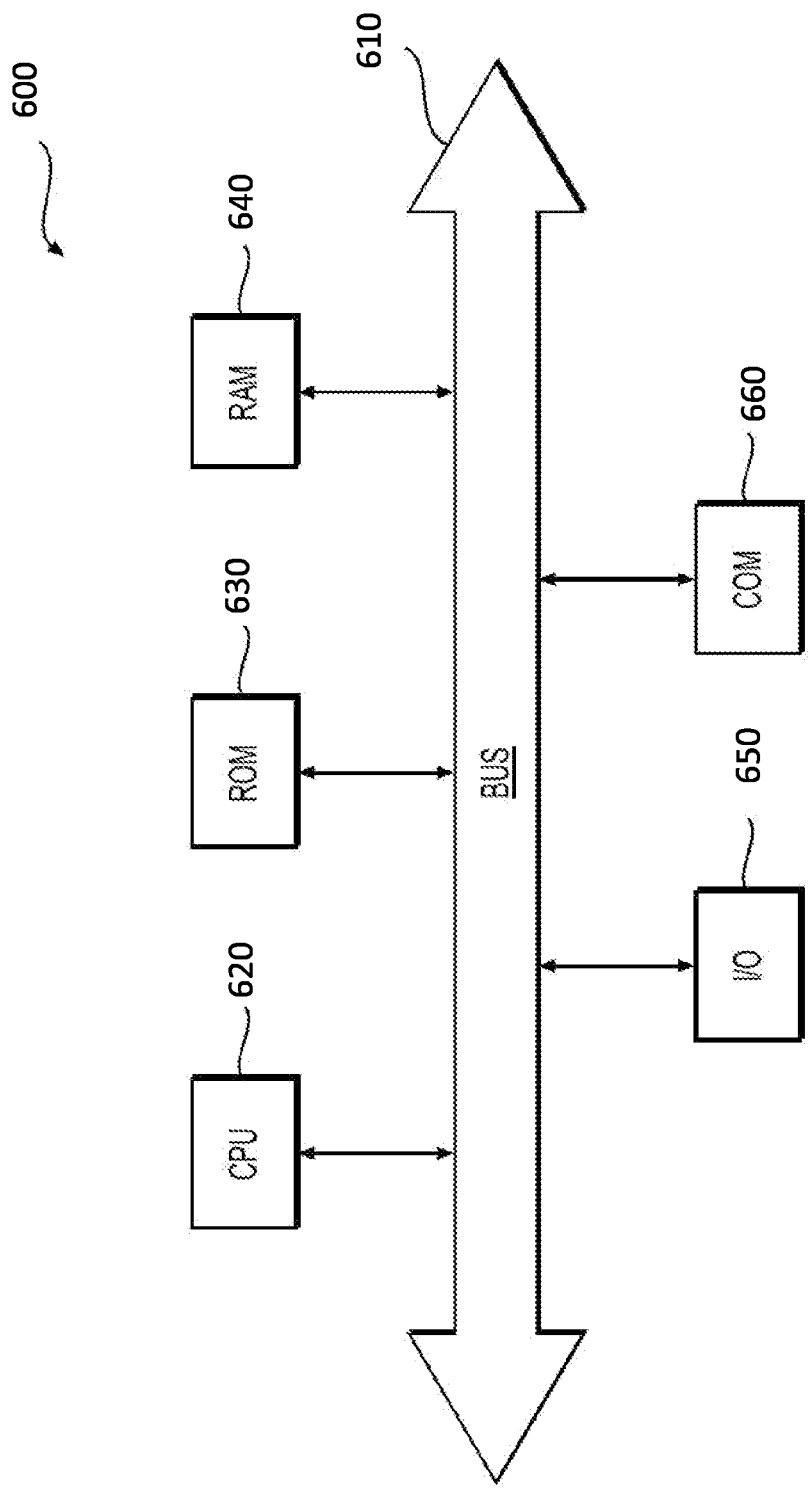
FIG. 6 depicts an example system that may execute techniques presented herein.

As shown in FIG. 6, device 600 may include a central processing unit (CPU) 620. CPU 620 may be any type of processor device including, for example, any type of special purpose or a general-purpose microprocessor device. As will be appreciated by persons skilled in the relevant art, CPU 620 also may be a single processor in a multi-core/multi-processor system, such system operating alone, or in a cluster of computing devices operating in a cluster or server farm. CPU 620 may be connected to a data communication infrastructure 610, for example, a bus, message queue, network, or multi-core message-passing scheme.

Device 600 also may include a main memory 640, for example, random access memory (RAM), and also may include a secondary memory 630. Secondary memory 630, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 630 may include other similar means for allowing computer programs or other instructions to be loaded into device 600. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 600.

Device 600 also may include a communications interface ("COM") 660. Communications interface 660 allows software and data to be transferred between device 600 and external devices. Communications interface 660 may include a modem, a network interface (such as an Ethernet card), a communications port, a PCMCIA slot and card, or the like. Software and data transferred via communications interface 660 may be in the form of signals, which may be electronic, electromagnetic, optical, or other signals capable of being received by communications interface 660. These signals may be provided to communications interface 660 via a communications path of device 600, which may be implemented using, for example, wire or cable, fiber optics, a phone line, a cellular phone link, an RF link or other communications channels.

Device 600 also may include input and output ports 650 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware.

The tools, modules, and functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples be considered as exemplary only.

What is claimed is:

1. A system for processing images, the system comprising:
    at least one memory storing instructions; and
    at least one processor configured to execute the instructions to perform operations comprising:
        receiving an image of a slide comprising a sample of tissue from a patient;
        providing the image as an input image to a trained convolutional neural network (CNN) to obtain a segmentation output image from the trained CNN, the segmentation output image assigning a tissue type from a plurality of tissue types to each pixel in the input image, wherein the CNN is trained based on a training data set including a plurality of training images comprising samples of tissue and, for each of the plurality of training images, corresponding segmentation labels of a tissue type from the plurality of tissue types assigned to each pixel of the respective training image;
determining one or more tests are to be performed on the tissue based on at least one tissue type in the segmentation output image; and
automatically ordering the one or more tests.

2. The system of claim 1, wherein the system further comprises a data storage device configured to store patient data, including the image.

3. The system of claim 1, wherein the slide comprising the sample of tissue is stained with hematoxylin and eosin.

4. The system of claim 1, wherein the plurality of tissue types include a background where no tissue is identified.

5. The system of claim 1, wherein the plurality of tissue types include one or more tissue types associated with tumors.

6. The system of claim 5, wherein the one or more tissue types associated with tumors include at least one of a tumor predisposition type or a tumor type.

7. The system of claim 6, wherein the at least one tissue type in the segmentation output image includes the at least one of the tumor predisposition type or the tumor type, and the one or more tests determined to be performed and automatically ordered include one or more panels associated with the at least one of the tumor predisposition type or the tumor type.

8. The system of claim 1, the operations further comprising:
identifying a diagnosis and/or a tissue morphology based on the at least one tissue type in the segmentation output image.

9. The system of claim 8, wherein the determining the one or more tests are to be performed on the tissue is further based on the identified diagnosis and/or tissue morphology.

10. The system of claim 8, wherein at least the diagnosis is identified, and the identified diagnosis comprises lung adenocarcinoma, breast carcinoma, endometrioid adenocarcinoma, colonic adenocarcinoma, adenocarcinoma in other tissues, sarcomas, prognostic biomarkers, suspicious lesions, amyloid presence, and/or fungal organisms.

11. The system of claim 8, wherein at least the tissue morphology is identified, and the identified tissue morphology comprises a BRCA1-associated protein 1 (BAP1) deficient nevi and/or a succinate dehydrogenase deficient tumor.

12. The system of claim 8, wherein the determining the one or more tests are to be performed on the tissue comprises:
determining a type of the one or more tests and/or slide parameters associated with the type of the one or more tests that are to be performed based on the identified diagnosis and/or tissue morphology.

13. The system of claim 1, wherein the one or more tests comprise different staining of the tissue, different cuts of the tissue, genomic tests, genetic tests, in-vitro lab tests, radiology imaging, and/or computational diagnostic tests.

14. A method for processing images, the method comprising:
receiving an image of a slide comprising a sample of tissue from a patient;
providing the image as an input image to a trained convolutional neural network (CNN) to obtain a segmentation output image from the trained CNN, the segmentation output image assigning a tissue type from a plurality of tissue types to each pixel in the input image, wherein the CNN is trained based on a training data set including a plurality of training images comprising samples of tissue and, for each of the plurality of training images, corresponding segmentation labels of a tissue type from the plurality of tissue types assigned to each pixel of the respective training image;
determining one or more tests are to be performed on the tissue based on at least one tissue type in the segmentation output image; and
automatically ordering the one or more tests.

15. The method of claim 14, wherein the slide comprising the sample of tissue is stained with hematoxylin and eosin.

16. The method of claim 14, wherein the plurality of tissue types include a background where no tissue is identified.

17. The method of claim 14, wherein the plurality of tissue types include one or more tissue types associated with tumors, and the one or more tissue types associated with tumors include at least one of a tumor predisposition type or a tumor type.

18. The method of claim 17, wherein the at least one tissue type in the segmentation output image includes one of the one or more tissue types associated with tumors, and the method further comprises:
identifying a diagnosis and/or a tissue morphology based on the at least one tissue type in the segmentation output image.

19. The method of claim 18, wherein the determining the one or more tests are to be performed on the tissue is further based on the identified diagnosis and/or tissue morphology, and the determining the one or more tests further comprises:
determining a type of the one or more tests and/or slide parameters associated with the type of the one or more tests that are to be performed based on the identified diagnosis and/or tissue morphology.

20. A non-transitory computer-readable medium storing instructions that, when executed by processor, cause the processor to perform operations for processing images, the operations comprising:
receiving an image of a slide comprising a sample of tissue from a patient;
providing the image as an input image to a trained convolutional neural network (CNN) to obtain a segmentation output image from the trained CNN, the segmentation output image assigning a tissue type from a plurality of tissue types to each pixel in the input image, wherein the CNN is trained based on a training data set including a plurality of training images comprising samples of tissue and, for each of the plurality of training images, corresponding segmentation labels of a tissue type from the plurality of tissue types assigned to each pixel of the respective training image;
determining one or more tests are to be performed on the tissue based on at least one tissue type in the segmentation output image; and
automatically ordering the one or more tests.

* * * * *